(12) United States Patent
Smith et al.

(10) Patent No.: US 11,299,405 B2
(45) Date of Patent: *Apr. 12, 2022

(54) PURIFICATION APPARATUS WITH ELECTRODELESS BULB AND METHODS OF OPERATION

(71) Applicant: NXP USA, Inc., Austin, TX (US)

(72) Inventors: Gavin James Smith, Chandler, AZ (US); Lionel Mongin, Chandler, AZ (US); Pierre Marie Jean Piel, Chandler, AZ (US)

(73) Assignee: NXP USA, Inc., Austin, TX (US)

( * ) Notice: Subject to any disclaimer, the term of this patent is extended or adjusted under 35 U.S.C. 154(b) by 814 days.

This patent is subject to a terminal disclaimer.

(21) Appl. No.: 15/719,485

(22) Filed: Sep. 28, 2017

(65) Prior Publication Data

US 2019/0092652 A1    Mar. 28, 2019

(51) Int. Cl.
*C02F 1/32* (2006.01)
*G01J 1/42* (2006.01)
(Continued)

(52) U.S. Cl.
CPC .............. *C02F 1/325* (2013.01); *A61L 9/20* (2013.01); *C02F 1/487* (2013.01); *G01J 1/429* (2013.01);
(Continued)

(58) Field of Classification Search
CPC .......... C02F 1/325; C02F 1/487; C02F 1/001; C02F 1/32; C02F 2201/3223;
(Continued)

(56) References Cited

U.S. PATENT DOCUMENTS 3,993,927 A    11/1976    Haugsjaa et al.
4,001,632 A    1/1977    Haugsjaa et al.
(Continued)

FOREIGN PATENT DOCUMENTS

EP    0 313 028 B1    7/1995
GB    315369 A    10/1930
(Continued)

OTHER PUBLICATIONS

Notice of Allowance; U.S. Appl. No. 15/719,482; 10 pages (dated Jul. 10, 2019).

(Continued)

*Primary Examiner* — Akash K Varma
(74) *Attorney, Agent, or Firm* — Sherry Gourlay (57) ABSTRACT

A purification apparatus includes a radio frequency (RF) signal source that generates an RF signal, first and second electrodes, and a conduit. The first electrode receives the RF signal and converts it into electromagnetic energy that is radiated by the first electrode. The conduit includes input and output ports and a chamber. The input and output ports are in fluid communication with the chamber, and the chamber is configured to receive an electrodeless bulb. The chamber is defined by first and second boundaries that are separated by a distance that is less than the wavelength of the RF signal so that the chamber is sub-resonant. The first electrode is physically positioned at the first boundary, and the second electrode is physically positioned at the second boundary. The first and second electrodes and the chamber form a structure that capacitively couples the electromagnetic energy into an electrodeless bulb within the chamber.

18 Claims, 4 Drawing Sheets

(51) Int. Cl.
*H01J 65/04* (2006.01)
*C02F 1/48* (2006.01)
*A61L 9/20* (2006.01)
*C02F 1/00* (2006.01)

(52) U.S. Cl.
CPC ............ *H01J 65/046* (2013.01); *C02F 1/001* (2013.01); *C02F 2201/326* (2013.01); *C02F 2201/3223* (2013.01); *C02F 2201/3225* (2013.01); *C02F 2201/46175* (2013.01); *C02F 2201/48* (2013.01); *C02F 2303/04* (2013.01)

(58) Field of Classification Search
CPC ........ C02F 2201/3225; C02F 2201/326; C02F 2201/46175; C02F 2201/48; C02F 2201/46109; C02F 2201/4612; C02F 2303/04; C02F 1/00; C02F 1/48; C02F 2101/00; A61L 9/20; A61L 2/10; G01J 1/429; G01J 1/42; G01J 1/047; H01J 65/046; H01J 65/04; H01J 65/044; G09G 3/22; H01R 33/05
USPC ......................................................... 210/739
See application file for complete search history.

(56) References Cited

U.S. PATENT DOCUMENTS

| | | | |
|---|---|---|---|
| 4,041,352 A | 8/1977 | McNeill et al. | |
| 4,053,814 A | 10/1977 | Regan et al. | |
| 4,431,947 A | 2/1984 | Ferriss et al. | |
| 4,937,503 A | 6/1990 | Sigai et al. | |
| 5,019,750 A | 5/1991 | Godyak | |
| 6,162,406 A | 12/2000 | Michael | |
| 6,476,565 B1 | 11/2002 | Kaminski | |
| 6,693,382 B2 | 2/2004 | Little et al. | |
| 6,696,802 B1 | 2/2004 | Lezcano et al. | |
| 6,737,809 B2 | 5/2004 | Espiau et al. | |
| 8,169,152 B2 | 5/2012 | DeVincentis et al. | |
| 8,258,687 B2 | 9/2012 | Espiau et al. | |
| 8,344,625 B2 | 1/2013 | Espiau et al. | |
| 8,342,714 B1 | 5/2013 | Roe et al. | |
| 8,847,488 B2 | 9/2014 | Doughty | |
| 8,981,663 B2 | 3/2015 | Hollingsworth | |
| 9,224,568 B2 | 12/2015 | Doughty | |
| 9,236,238 B2 | 1/2016 | Espiau et al. | |
| 9,439,273 B2 | 9/2016 | Borsuk et al. | |
| 9,640,380 B1 | 5/2017 | Brockett et al. | |
| 9,754,777 B1 | 9/2017 | Matloubian et al. | |
| 9,805,925 B1 | 10/2017 | Brockett et al. | |
| 9,875,887 B1 | 1/2018 | Brockett et al. | |
| 10,125,032 B2 | 11/2018 | Egner et al. | |
| 2002/0047615 A1 | 4/2002 | Yokozeki et al. | |
| 2003/0206833 A1* | 11/2003 | Obee ........................ | C02F 1/325 422/121 |
| 2008/0054813 A1 | 3/2008 | Espiau et al. | |
| 2008/0264875 A1* | 10/2008 | NeCamp ................... | C02F 1/325 210/748.11 |
| 2010/0253231 A1 | 10/2010 | Devincentis et al. | |
| 2010/0283389 A1* | 11/2010 | Frederick .............. | H01J 65/044 315/39 |
| 2010/0295453 A1 | 11/2010 | DeVincentis et al. | |
| 2011/0043123 A1 | 2/2011 | Gilliard et al. | |
| 2011/0204784 A1* | 8/2011 | Espiau .................. | H01J 65/044 315/39 |
| 2012/0014118 A1 | 1/2012 | Espiau et al. | |
| 2012/0161031 A1* | 6/2012 | NeCamp ................. | C02F 1/325 250/429 |
| 2012/0286664 A1 | 11/2012 | Espiau et al. | |
| 2013/0040529 A1 | 2/2013 | Guthrie et al. | |
| 2014/0117848 A1 | 5/2014 | Meyer | |
| 2014/0125225 A1 | 5/2014 | Calame et al. | |
| 2014/0145601 A1 | 5/2014 | Goscha et al. | |
| 2014/0145606 A1 | 5/2014 | Goscha et al. | |
| 2014/0368109 A1 | 12/2014 | Goscha et al. | |

FOREIGN PATENT DOCUMENTS

| | | | | |
|---|---|---|---|---|
| GB | 2 399 216 A | | 9/2004 | |
| GB | 2399216 A | * | 9/2004 | ................ C02F 1/32 |
| WO | 2013/136187 A2 | | 9/2013 | |
| WO | 2015/162089 A1 | | 10/2015 | |

OTHER PUBLICATIONS

Non Final Office Action; U.S. Appl. No. 15/179,482; 18 pages (dated Dec. 13, 2018).

U.S. Appl. No. 15/719,482; not yet published; 37 pages (dated Sep. 28, 2017).

"UV Water Purifier Comparison", The UV Application Specialist, pp. 1-6, retrieved from the internet Aug. 29, 2017 at: https://ultraviolet.com/uv-water-purifier-comparison/ (Jun. 15, 2017).

* cited by examiner

FIG. 7

PURIFICATION APPARATUS WITH ELECTRODELESS BULB AND METHODS OF OPERATION

TECHNICAL FIELD

Embodiments of the subject matter described herein relate generally to purification apparatus, and more particularly to liquid or air purification apparatus that utilize ultraviolet light to kill pathogens.

BACKGROUND

Pathogens (e.g., bacterium, viruses, fungi, and other microorganisms) are present in consumable water throughout the world, potentially causing illness in those who consume untreated water. Some conventional water purification systems utilize lethal dosages of ultraviolet (UV) light to kill pathogens in water (e.g., a minimum lethal dosage up to 160,000 µs/cm$^2$).

Conventional UV water purification systems use electrode-based lamps and ballasts (e.g., high voltage striking sources) to produce the UV light. An undesirable characteristic of such a system is that electrode-based lamps have a relatively short operational lifetime, ranging from 10,000-20,000 hours (50-100 days). Thus, the electrode-based lamps must be replaced frequently, adding to the operational expenses of the system. In addition, the electrodes within electrode-based lamps begin to degrade after extended operation. Degradation of the lamps may create a black film inside the bulb, which may result in significantly lower UV light output and less effective purification.

In addition, in such systems, the ballast is known to heat up under continuous operation, and this tendency is exacerbated in hotter environments. Excessive ballast heating may result in system failures. Further, because a conventional ballast is characterized by a timing gap (e.g., 30 seconds or more) between startup to a full lamp UV output state, another undesirable characteristic of conventional systems is slow startup time.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the words "exemplary" and "example" mean "serving as an example, instance, or illustration." Any implementation described herein as exemplary or an example is not necessarily to be construed as preferred or advantageous over other implementations. Furthermore, there is no intention to be bound by any expressed or implied theory presented in the preceding technical field, background, or the following detailed description.

Embodiments of the subject matter described herein relate to liquid purification systems in which radio frequency (RF) energy is capacitively coupled into an electrodeless bulb, resulting in the bulb producing ultraviolet (UV) light. The electrodeless bulb is positioned in a conduit through which the liquid is transferred. More specifically, the electrodeless bulb is positioned in the conduit between two electrodes: an "active electrode" (or anode); and a "grounded electrode" (or cathode). The active and grounded electrodes essentially function as capacitor plates, and the liquid in the conduit plus the electrodeless bulb essentially function as the capacitor dielectric. The conduit is at least partially defined by the distance between the two electrodes, and that distance is less than one wavelength for the range of operational frequencies of the system. Accordingly, the conduit is quasi-resonant (or sub-resonant) within the operational frequency range.

An RF signal source provides an RF signal to the active electrode. The grounded electrode is electrically coupled to ground or to a voltage reference other than ground. According to an embodiment, the frequency of the RF signal provided to the active electrode is significantly lower than frequencies used to excite electrodeless bulbs in conventional systems. For example, conventional systems may radiate RF signals at frequencies of 1000 megahertz (MHz) and higher in order to excite the gasses within an electrodeless bulb. In contrast, embodiments of liquid purification systems described herein may utilize RF signals at frequencies of 300 MHz or less, and with the above-described system configuration, these lower frequencies are sufficient to excite the gasses within the electrodeless bulbs due to the capacitive coupling of the RF energy into the bulb. Because embodiments of the system configuration enable RF signals to be used with relatively low operational frequencies, the system may have significantly higher efficiency than is possible with conventional systems.

Embodiments further include a feedback and control sub-system, and a variable resonant circuit coupled between the RF signal source and the active electrode. The feedback and control sub-system may continuously or periodically monitor the intensity of the electric field within the conduit (or the luminous/radiation intensity or the pathogen level), and may dynamically reconfigure the variable resonant circuit to ensure that high efficiency operation is achieved throughout system operation (e.g., including through the system start-up process during which the bulb resonance may vary significantly). More specifically, based on feedback indicating the electric field intensity (or luminous/radiation intensity or pathogen level) within the conduit, a system controller may alter passive component values within the variable resonant circuit to better match the variable resonance of the bulb(s), which in turn may cause the electric field intensity to increase or decrease, thus increasing or decreasing the intensity of light or radiation emitted by each electrodeless lamp tube. This adaptive resonance control may enable the system to achieve optimal performance (e.g., highest efficiency and/or highest luminous/radiation output) throughout all phases of operation, and additionally may facilitate reductions in system start-up time.

As will be described in more detail later, the various embodiments may be incorporated into a variety of different types of systems to achieve different results. For example, embodiments of liquid purification systems discussed herein may be incorporated into water purification systems, such as stand-alone water purification units, wastewater treatment systems, and appliances that dispense or utilize water (e.g., refrigerator units, and so on).

Figure 1:
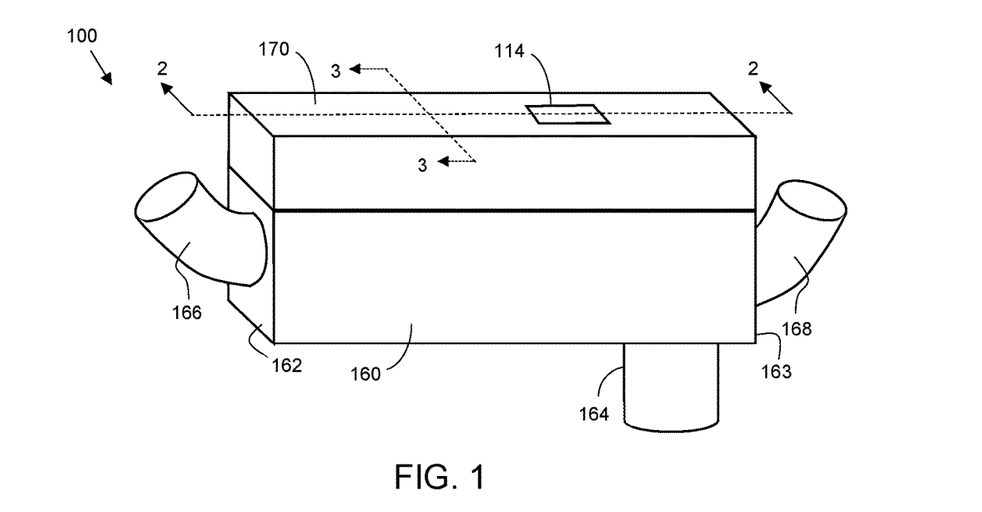
FIG. 1 is a perspective view of a liquid purification apparatus, in accordance with an example embodiment.
Figure 2:
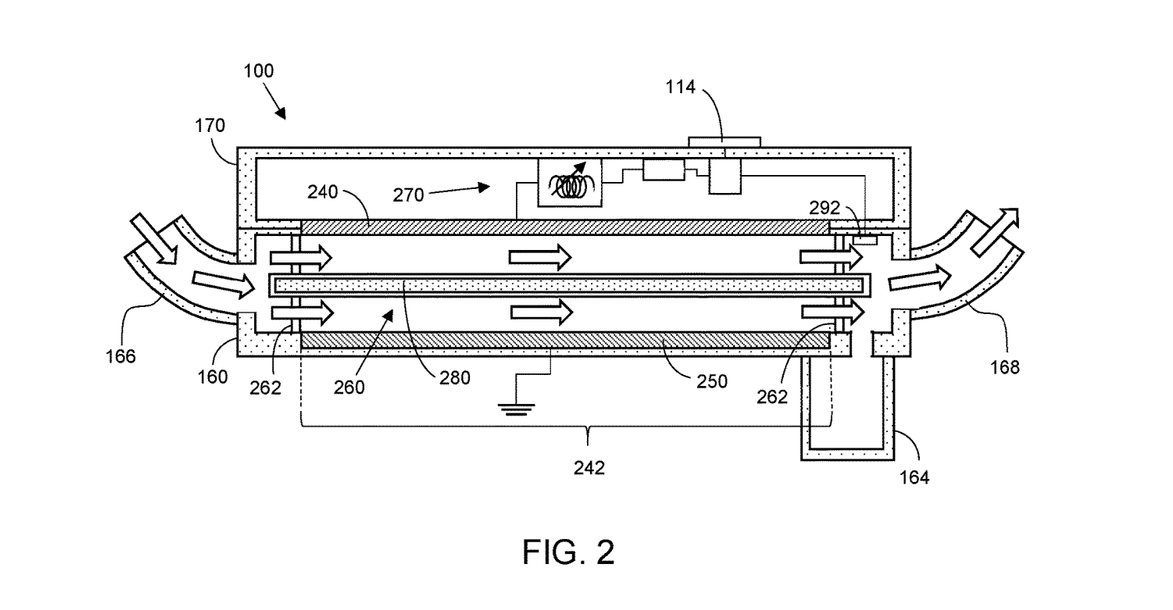
FIG. 2 is a cross-sectional side view of a portion of a liquid purification system along line 2-2 of FIG. 1, in accordance with an example embodiment.
Figure 3:
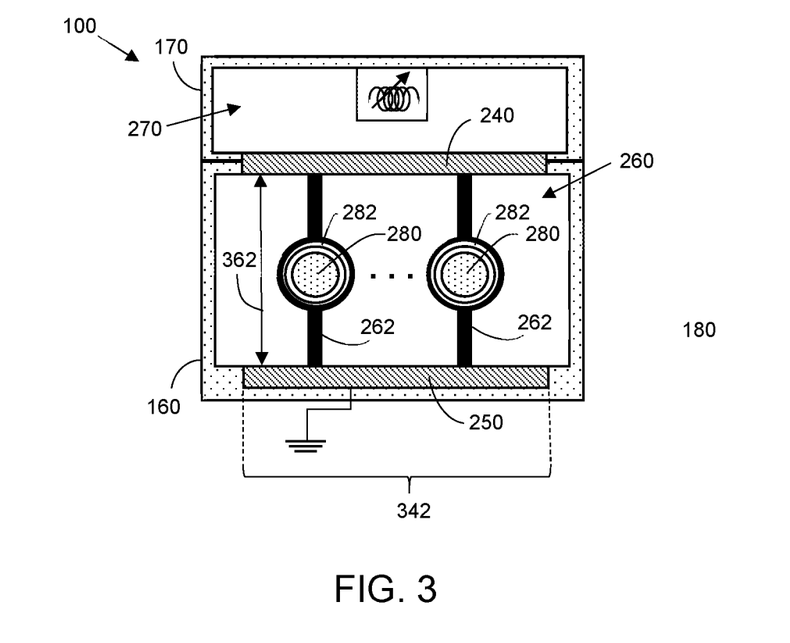
FIG. 3 is a cross-sectional, side view of a portion of a liquid purification system along line 3-3 of FIG. 1, in accordance with an example embodiment.

FIG. 1 is a perspective view of a liquid purification system 100, in accordance with an example embodiment. FIG. 1 should be viewed in conjunction with FIGS. 2 and 3, which include various cross-sectional views of the liquid purification system 100. More specifically, FIG. 2 is a cross-sectional side view of a portion of the liquid purification system 100 along line 2-2 of FIG. 1, and FIG. 3 is a cross-sectional side view of a portion of the liquid purification system 100 along line 3-3 of FIG. 1.

Liquid purification system 100 includes an RF signal source and controller subsystem 170 (herein "RF subsystem"), a lamp containment and excitation conduit 160 (herein "lamp conduit"), and a user interface 114. The user interface 114 may include one or more buttons, dials, keys, displays, and/or other features that enable a user to input information into the system regarding system operational parameters, and so on, and that provide user-perceptible information that enables the user to monitor system operation, and so on.

The lamp conduit 160 includes an input port 166, an output port 168 and an interior chamber 260. Liquid (e.g., water or other liquids) may flow into the input port 166, through the interior chamber 260, and out of the output port 168. As will be described below, UV light produced by one or more electrodeless bulbs 240, 250 within the interior chamber 260 may purify the liquid as it passes over one or more electrodeless bulbs 280 while traveling through the lamp conduit 160. More specifically, the UV light may kill pathogens (e.g., bacterium, viruses, fungi, and other microorganisms) in the liquid. In an embodiment, the lamp conduit 160 also may include a removable and/or replaceable receptacle or filter 164 in fluid communication with the interior chamber 260, which is used to filter out and/or collect the dead pathogens in whichever medium is transmitted through the interior chamber 260.

Figure 4:
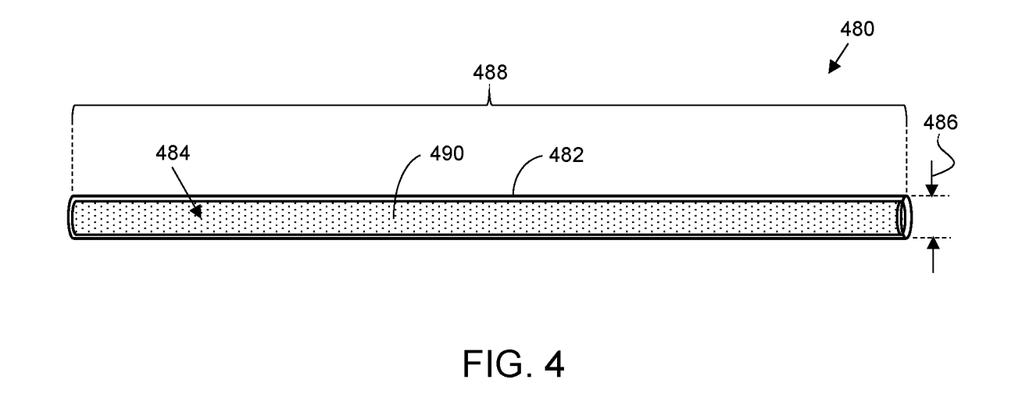
FIG. 4 is a cross-sectional side view of an electrodeless bulb, in accordance with an example embodiment.

Within the interior chamber 260 the lamp excitation conduit 160 is configured to hold first and second electrodes 240, 250 in a fixed physical position with respect to each other. Accordingly, the electrodes 240, 250 are positioned on opposing sides of the interior chamber 260. One or more electrodeless bulbs 280 are positioned within the interior chamber 260 between the electrodes 240, 250. For example, the electrodeless bulb(s) 280 may be held in position with one or more support structures 262 disposed along the length of the interior chamber 260. For example, as depicted in FIG. 3, the lamp support components 262 may include circular clamps with interior diameters that are about equal to the diameter of the electrodeless bulb(s) 280. Posts may physically couple the clamps to the walls of the interior chamber 260. Other embodiments may include differently configured lamp support components. In some embodiments, the electrodeless bulb(s) 280 may be covered with a protective sleeve 282 (e.g., formed from quartz or another suitable material), which may protect the bulb(s) 280 from damage, and may prevent leakage of the materials within the bulb(s) 280 into the liquid within the chamber 260 in the event that a bulb 280 is broken during operation. Although the example embodiment shown in FIG. 3 includes two bulbs 280, alternate embodiments may have any number of bulbs in a range of one bulb to 50 bulbs or more.

The RF subsystem 170 includes an excitation circuit 270 (e.g., including components discussed later in conjunction with RF subsystem 510, FIG. 5). The excitation circuit 270 is electrically coupled to the first electrode 240, and the second electrode 250 is electrically coupled to an electrical ground reference, in an embodiment. According to an embodiment, each of the first and second electrodes 240, 250 is formed from an elongated conductive component, which extends between first and second ends 162, 163 of the lamp conduit 160. Each electrode 240, 250 may include a planar conductive structure, for example, which is at least partially defined by a length 242 and a width 342. Desirably, the first and second electrodes 240, 250 have lengths 242 that are approximately as long as a length (e.g., length 488, FIG. 4) of the electrodeless bulbs 280 so that the entire length of each electrodeless bulb 280 may be positioned in the interior chamber 260 directly between the first and second electrodes 240, 250. In other embodiments, the electrodeless bulbs 280 may be significantly longer or shorter than either or both of the first and/or second electrodes 240, 250. In various embodiments, the lengths 242 of the electrodes 240, 250 and/or the length of the electrodeless bulb(s) 280 may be in a range of about 5 centimeters (cm) to about 1.5 meters, although the lengths may be smaller or larger, as well. The widths 342 of the electrodes 240, 250 may be in a range of about 2 cm to about 1.0 meters, although the widths may be smaller or larger, as well. For example, each electrode 240, 250 may be formed from a homogenous conductive material (e.g., copper or another conductive material). In other embodiments, each electrode 240, 250 may be a composite structure with a conductive outer surface.

The first and second electrodes 240, 250 are separated across the interior chamber 260 by a distance 362, which corresponds to one dimension of the interior chamber 260. Essentially, the first and second electrodes 240, 250 at least partially bound the interior chamber 260, where the chamber-facing surface of the first electrode 240 is one boundary, and the chamber-facing surface of the second electrode 250 is a second boundary. In various embodiments, the distance 362 is in a range of about 0.10 meters to about 1.0 meter, although the distance may be smaller or larger, as well.

The excitation circuit 270 is configured to produce an RF signal, which is conveyed to the first electrode 240 through a conductor. The first electrode 240 is configured to radiate electromagnetic energy into the interior chamber 260 in response to receiving the RF signal. Accordingly, the first electrode 240 generates an electric field that extends into the interior chamber 260 (and thus through the electrodeless bulb(s) 280) to impinge on the second electrode 250.

In an embodiment, the excitation circuit 70 is configured to produce the RF signal at an operational frequency in a range of about 10 MHz to about 100 MHz, or a range of about 100 MHz to about 3.0 gigahertz (GHz), although the range of operational frequencies may be different, in other embodiments. As discussed above, the first and second electrodes 240, 250 are separated across the interior chamber 260 by distance 362. For example, the distance 362 may be in a range of about 10 centimeters (cm) to about 3.0 meters or more. According to an embodiment, distance 362 is less than the wavelength of the RF signal produced by the excitation circuit 270. In other words, the interior chamber 260 is a sub-resonant chamber. In some embodiments, the distance 362 is less than about half the wavelength of the RF signal. In other embodiments, the distance 362 is less than about one quarter the wavelength of the RF signal. In still other embodiments, the distance 362 is less than about one eighth the wavelength of the RF signal. In still other embodiments, the distance 362 is less than about one 50th the wavelength of the RF signal. In still other embodiments, the distance 362 is less than about one 100th the wavelength of the RF signal.

In general, a system 100 designed for lower operational frequencies (e.g., frequencies between 10 MHz and 100 MHz) may be designed to have a distance 362 that is a smaller fraction of the wavelength. For example, when system 100 is designed to produce an RF signal with an operational frequency of about 10 MHz (corresponding to a wavelength of about 30 meters), and distance 362 is selected to be about 0.5 meters, the distance 362 is about one 60th the wavelength of the RF signal. Conversely, when system 100 is designed for an operational frequency of about 300 MHz (corresponding to a wavelength of about 1 meter), and distance 362 is selected to be about 0.5 meters, the distance 362 is about one half the wavelength of the RF signal.

With the operational frequency and the distance 362 between electrodes 240, 250 being selected to define a sub-resonant interior chamber 260, electromagnetic energy radiated by the first electrode 240 is capacitively coupled into the electrodeless bulb(s) 280. Accordingly, the first electrode 240 may be analogized to a first plate of a capacitor, the second electrode 250 may be analogized to a second plate of a capacitor, and the liquid within the interior chamber 260 plus the electrodeless bulb(s) 280 may be analogized to a capacitor dielectric. Accordingly, the first electrode 240 alternatively may be referred to herein as an "anode" or "active electrode," and the second electrode 250 may alternatively be referred to herein as a "cathode" or "grounded electrode."

Essentially, the voltage across the first and second electrodes 240, 250 enables activation of the electrodeless bulb(s) 180. According to various embodiments, the excitation circuit 270 is configured to generate the RF signal to produce voltages across the electrodes 240, 250 in a range of about 90 volts to about 3000 volts, although the system may be configured to produce lower or higher voltages across electrodes 240, 250, as well. At relatively low voltages, each electrodeless bulb 280 may begin to emit light/radiation, and as the voltage is increased, the intensity of the light/radiation also increases up until the electrodeless bulb 280 is saturated (i.e., the luminous/radiation intensity reaches a plateau and does not increase with increasing voltage).

Figure 5:
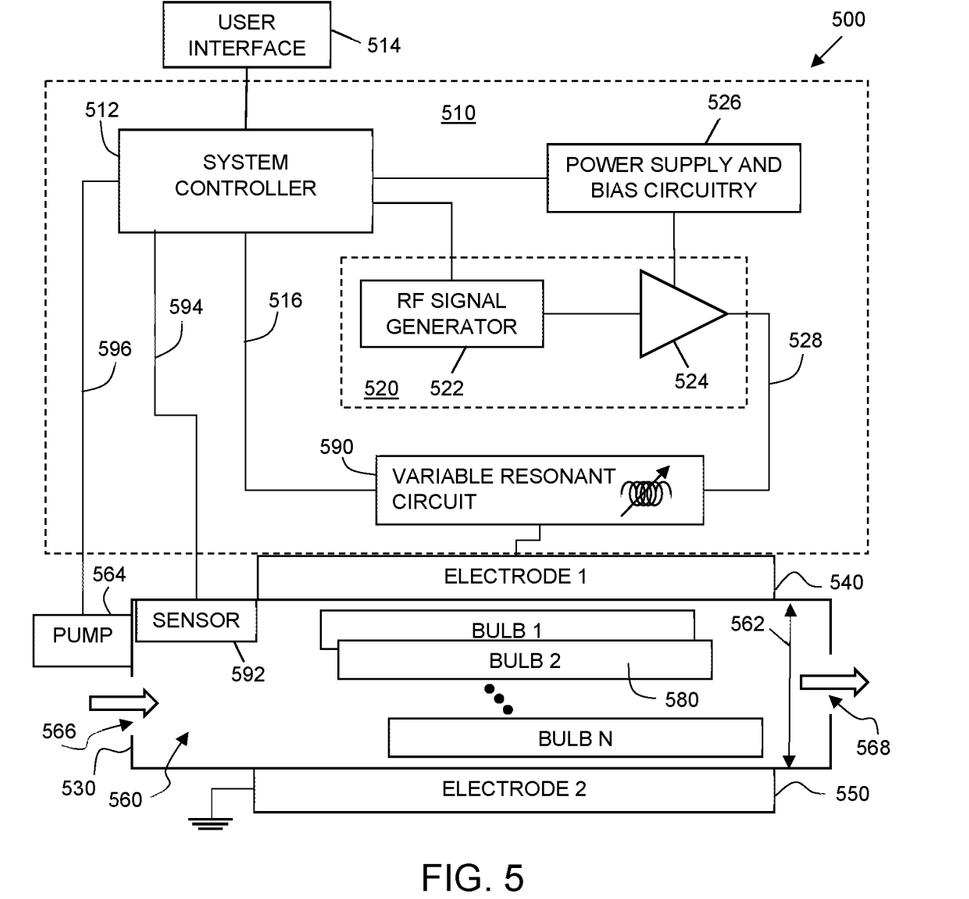
FIG. 5 is a simplified block diagram of a liquid purification system, in accordance with an example embodiment.

According to an embodiment, the system 100 also may include a feedback and control subsystem that includes a variable resonant circuit (e.g., variable resonant circuit 590, 600, FIGS. 5, 6), a sensor 292 (e.g., an electric field and/or light/radiation sensor, such as sensor 592, FIG. 5), and a feedback circuit (e.g., including feedback path 594, FIG. 5). As will be explained in more detail later, the variable resonant circuit, which is electrically coupled between the excitation circuit 270 and the first electrode 240, is configured to resonate at and near the resonance of the electrodeless bulb(s) 280, and to provide an impedance transformation between the output impedance of the excitation circuit 270 and the input impedance of the first electrode 240 (plus the interior chamber 260 and the electrodeless bulb(s) 280). The sensor 292 is located within or in proximity to the interior chamber 260, and is configured to sense an electric field intensity within the interior chamber 260 and/or an intensity of light/radiation emitted by the electrodeless bulb(s) 280. The feedback circuit is electrically coupled between the sensor 292 and the excitation circuit 270, and is configured to convey a feedback signal indicating the sensed intensity to the excitation circuit 270. Based on the feedback signal, a controller (e.g., controller 512, FIG. 5) within the excitation circuit 270 may alter the characteristics of the RF signal provided to the first electrode 240. For example, the controller may vary the RF signal frequency or amplitude. In addition or alternatively, the controller may send control signals to the variable resonant circuit to change the resonant frequency of the variable resonant circuit to better match the current resonant frequency of the bulb(s) 280. The resonant frequency of the electrodeless bulbs 280 may vary during system startup and operation. According to an embodiment, and as will be described in more detail later in conjunction with FIG. 7, the feedback and control subsystem may enable the system 100 to operate efficiently throughout all phases of operation by altering the resonant frequency of the variable resonant circuit based on the sensed electric field and/or luminous/radiation intensities.

FIG. 4 is a cross-sectional side view of an electrodeless bulb 480 (e.g., electrodeless bulb 280, FIG. 2) that may be suitable for use in system 100, in accordance with an example embodiment. Electrodeless bulb 480 is a gas discharge bulb, which includes a hermetically sealed, hollow transparent sleeve 482 (defining a chamber 484) that encloses a gas 490. According to an embodiment, the chamber 484 is completely sealed, and is devoid of internal electrodes or other components.

For example, the transparent sleeve 482 may be formed from quartz, glass, crystalline material, or other suitable materials. One or more films or coatings (not shown) may be disposed on the inner and/or outer surfaces of the sleeve 482. The sleeve 482 dimensions are defined by an outer diameter 486 and a length 488. For example, the diameter 486 may be in a range of about 1 cm to about 2.5 cm, and the length 488 may be in a range of about 5 cm to about 1.5 meters, in various embodiments. In other embodiments, the diameter 486 and/or length 488 may be larger and/or smaller than the above-given example ranges. In addition, although the embodiment of sleeve 482 in FIG. 4 has a straight tubular shape, the shape of the sleeve 482 may be different, as well. For example, other embodiments of a sleeve may be curved, the diameter of the sleeve may vary along its length, the sleeve may have an annular ring shape, and so on.

The gas 490 contained within the sleeve 482 may include one or more ionized noble gasses (e.g., argon, neon, krypton, xenon), which are configured to emit light (or radiation) when irradiated with microwave energy. In various embodiments, the gas 490 within bulb 480 may be configured to output ultraviolet radiation. For example, when appropriately irradiated, the gas 490 may have significant spectral output intensities at wavelengths in a range of about 100 nanometers (nm) to about 400 nm. In such embodiments, the system (e.g., system 100) within which the bulb 480 is used may be configured to purify air, liquids (e.g., water), slurries, or other mediums that come into proximity or contact with the bulb 480 or system.

One or more additional substances, which vaporize during startup to become part of gas 490, also may be contained within the sleeve 482. For example, such additional materials may include mercury, sodium, sulfur, gallium, iron, indium, metal halides, and/or other suitable materials. The additional material(s) may alter the spectral output of the gas 490.

FIG. 5 is a simplified block diagram of a liquid purification system 500 (e.g., system 100, FIG. 1), in accordance with an example embodiment. It should be understood that FIG. 5 is a simplified representation of a liquid purification system 500 for purposes of explanation and ease of description, and that practical embodiments may include other devices and components to provide additional functions and features, and/or the liquid purification system 500 may be part of a larger electrical system.

Liquid purification system 500 includes an RF subsystem 510 (e.g., RF subsystem 170, FIG. 1), a user interface 514 (e.g., user interface 114, FIG. 1), and a lamp conduit 530 (e.g., lamp conduit 160, FIG. 1). According to an embodiment, system 500 also includes a variable resonant circuit 590 electrically coupled between an output of the RF subsystem 510 and the lamp conduit 530. Further, system 500 may include a sensor 592 and a feedback path 594, which is configured to provide sensor signals that are used by the RF subsystem 510 to control the variable resonant circuit 590. Further still, the system 500 may include a pump 564, which is configured to facilitate the flow of liquid through the lamp conduit 530.

User interface 514 may correspond to a control panel, for example, which enables a user to activate the system 500, and to provide inputs regarding operational parameters (e.g., the duration of system activation, liquid flow rate, and so on). In addition, the user interface may be configured to provide user-perceptible outputs indicating the operational status of the system and other information.

The RF subsystem 510 includes a system controller 512, an RF signal source 520, power supply and bias circuitry 526, and the variable resonant circuit 590, in an embodiment. In alternate embodiments, the RF subsystem 510 may have multiple RF signal sources and/or power supply and bias circuits. System controller 512 may include one or more general purpose or special purpose processors (e.g., a microprocessor, microcontroller, Application Specific Integrated Circuit (ASIC), and so on), volatile and/or non-volatile memory (e.g., Random Access Memory (RAM), Read Only Memory (ROM), flash, various registers, and so on), one or more communication busses, and other components. According to an embodiment, system controller 512 is coupled to user interface 514, RF signal source 520, power supply and bias circuitry 526, variable resonant circuit 590, sensor 592 (if included), and pump 564 (if included). System controller 512 is configured to receive signals indicating user inputs received via user interface 514, and to receive sensor signals from sensor 592. Responsive to the received signals and measurements, and as will be described in more detail later, system controller 512 provides control signals to the power supply and bias circuitry 526 and to the RF signal generator 522 of the RF signal source 520. In addition, system controller 512 provides control signals to the variable resonant circuit 590 (over path 516), which cause the circuit 590 to change its state or configuration. Finally, system controller 512 may provide control signals to pump 564 (over path 596), which cause the pump 564 to pump liquid through the lamp conduit 530 at a desired flow rate.

The lamp excitation conduit 530 includes an input port 566 (e.g., port 166, FIG. 1), an interior chamber 560 (e.g., interior chamber 260, FIG. 2), and an output port 568 (e.g., output port 168, FIG. 1). First and second electrodes 540, 550 (e.g., electrodes 240, 250, FIG. 1) are positioned in a fixed physical relationship with respect to each other on either side of the interior chamber 560 (e.g., interior chamber 260, FIG. 2). One or more electrodeless bulbs 580 (e.g., bulbs 280, FIG. 2) are positioned within the interior chamber 560 between the electrodes 540, 550. As discussed previously, a distance 562 between the electrodes 540, 550 renders the interior chamber 560 a sub-resonant chamber.

An output of the RF subsystem 510, and more particularly an output of RF signal source 520, is electrically coupled to the first electrode 540 through a conductive transmission path 528, and through the variable resonant circuit 590. The second electrode 550 is electrically coupled to an electrical ground reference, in an embodiment. For example, the electrical ground reference may be coupled to the second electrode 550.

Interior chamber 560, the bulb(s) 580 positioned in the interior chamber 560, and any liquids or other media within the interior chamber 560 present a cumulative load for the electromagnetic energy (or RF power) that is radiated into the interior chamber 560 by the first electrode 540. More specifically, the interior chamber 560, the bulb(s) 580, and the media present an impedance to the system, referred to herein as a "conduit input impedance." The conduit input impedance changes during a purification operation as the operational state of the bulb(s) 580 changes. In addition, the conduit input impedance may change as the characteristics of any media (e.g., air, water, or other media) within the interior chamber 560 changes. According to an embodiment, sensor 592 sends sensor signals over feedback path 594 to the system controller 512, which indicate sensed electromagnetic field intensity and/or luminous/radiation intensity within or proximate to the interior chamber 560. In response to receiving the sensor signals, the system controller 512 may alter the state of the variable resonant circuit 590. More specifically, the system controller 512 may provide control signals over control path 516 to the variable resonant circuit 590, which cause the variable resonant circuit 590 to vary the inductive, capacitive, and/or resistive values of one or more components within the circuit 590, thus adjusting the resonant frequency of the circuit 590. Adjustment of the resonant frequency to better match the then-current resonant frequency of the bulb(s) 580 may increase the luminous/radiation intensity within the interior chamber 560. In addition, the system 500 may be configured to provide frequency and/or phase adjustment to the RF signal, as well.

As mentioned above, the first electrode 540 is electrically coupled to the RF signal source 520 through the resonant circuit 590 (e.g., resonant circuit 600, FIG. 6) and a transmission path 528, in an embodiment. As will be described in more detail later, the resonant circuit 590 is configured to resonant at a frequency that is close to the resonant frequency of the bulb(s) 580. In an embodiment, the resonant circuit 590 includes a network of passive components (e.g., inductors, capacitors, resistors). In an embodiment, the resonant circuit 590 may be configured to have a maximum resonance within a frequency range that encompasses the resonant frequencies of the bulb(s) through all luminous states of the bulb(s). For example, the resonant circuit 590 may be configured to have a variable maximum resonance in a range of about 10.0 MHz to about 100 MHz and/or from about 100 MHz to about 3.0 GHz, although the maximum resonance may occur at frequencies outside of this range, as well.

The variable resonant circuit 590 may have any of a variety of configurations. For example, the circuit 590 may include any one or more circuits selected from an inductance/capacitance (LC) network, a series inductance network, a shunt inductance network, or a combination of bandpass, high-pass and low-pass circuits, in various embodiments. According to more specific embodiments, the variable resonant circuit 590 includes a variable inductance network (e.g., network 600, FIG. 6). The inductance, capacitance, and/or resistance values provided by the variable resonant circuit 590, which in turn affect the resonant frequency of the circuit 590, are established using control signals from the system controller 512, as will be described in more detail later. In any event, by changing the state of the variable resonant circuit 590 over the course of a purification operation to dynamically match the ever-changing bulb resonant frequency, the system efficiency may be maintained at a high level despite variations in the bulb resonant frequency during the purification operation.

According to an embodiment, RF signal source 520 includes an RF signal generator 522 and a power amplifier 524 (e.g., including one or more power amplifier stages). In response to control signals provided by system controller 512, RF signal generator 522 is configured to produce an oscillating electrical signal having a frequency in an ISM (industrial, scientific, and medical) band, although the system could be modified to support operations in other frequency bands, as well. The RF signal generator 522 may be controlled to produce oscillating signals of different power levels and/or different frequencies, in various embodiments. For example, the RF signal generator 522 may produce a signal that oscillates in a range of about 10.0 MHz to about 100 MHz and/or from about 100 MHz to about 3.0 GHz. Some desirable frequencies may be, for example, 13.56 MHz (+/−5 percent), 27.125 MHz (+/−5 percent), 40.68 MHz (+/−5 percent), and 2.45 GHz (+/−5 percent). Alternatively, the frequency of oscillation and/or the power level may be lower or higher than the above-given ranges or values.

The power amplifier 524 is configured to receive the oscillating signal from the RF signal generator 522, and to amplify the signal to produce a significantly higher-power signal at an output of the power amplifier 524. For example, the output signal may have a power level in a range of about 1 watt to about 1000 watts or more. The gain applied by the power amplifier 524 may be controlled using gate bias voltages and/or drain supply voltages provided by the power supply and bias circuitry 526 to each stage of amplifier 524. More specifically, power supply and bias circuitry 526 provides bias and supply voltages to each RF amplifier stage in accordance with control signals received from system controller 512.

In an embodiment, each stage of amplifier 524 is implemented as a power transistor, such as a field effect transistor (FET), having an input terminal (e.g., a gate or control terminal) and two current carrying terminals (e.g., source and drain terminals). Impedance matching circuits (not illustrated) may be coupled to the input (e.g., gate) and/or output (e.g., drain terminal) of some or all of the amplifier stages, in various embodiments. In an embodiment, each transistor of the amplifier stages includes a laterally diffused metal oxide semiconductor FET (LDMOSFET) transistor. However, it should be noted that the transistors are not intended to be limited to any particular semiconductor technology, and in other embodiments, each transistor may be realized as a gallium nitride (GaN) transistor, another type of MOSFET transistor, a bipolar junction transistor (BJT), or a transistor utilizing another semiconductor technology.

In FIG. 5, the power amplifier arrangement 524 is depicted to include one amplifier stage coupled in a particular manner to other circuit components. In other embodiments, the power amplifier arrangement 524 may include other amplifier topologies and/or the amplifier arrangement may include two or more amplifier stages. For example, the power amplifier arrangement may include various embodiments of a single ended amplifier, a double ended amplifier, a push-pull amplifier, a Doherty amplifier, a Switch Mode Power Amplifier (SMPA), or another type of amplifier.

As mentioned above, some embodiments of system 500 may include electromagnetic field sensor(s), ultraviolet radiation sensor(s), luminous intensity sensors, pathogen sensors, and/or other types of sensors 592. The sensor(s) 592 may be positioned in locations that enable the electromagnetic field intensity and/or the ultraviolet radiation intensity and/or the luminous intensity and/or the fluid contamination levels within the interior chamber 560 be sensed during a purification operation. When provided to the system controller 512 through the feedback path 594, the electromagnetic field intensity, and/or luminous/radiation intensity information, and/or pathogen level information enables the system controller 512 to alter the power of the RF signal supplied by the RF signal source 520 (e.g., by controlling the bias and/or supply voltages provided by the power supply and bias circuitry 526), and/or to adjust the state of the variable resonant circuit 590.

As discussed above, the resonant circuit 590 may be a fixed or variable resonant circuit, in various embodiments, which is used to match the dynamic resonance of the bulb(s) 580 to maximize, to the extent possible, the intensity of the light/radiation emitted by the bulb(s) 580. The initial resonant frequency of the bulb(s) 580 may not be known with accuracy at the beginning of a purification operation. Further, the resonant frequency of the bulb(s) 580 changes during a purification operation as the bulb(s) 580 transition from a fully off state to a fully on state (e.g., during system startup). According to an embodiment, the resonant circuit 590 is a variable resonant circuit, and the system controller 512 may provide control signals to the variable resonant circuit 590 that cause modifications to the state of the variable resonant circuit 590. This enables the system controller 512 to establish an initial state of the variable resonant circuit 590 (i.e., an initial resonant frequency) at the beginning of the purification operation and to modify the state of the variable resonant circuit 590 so that an adequate match between the circuit 590 and bulb 580 resonance may be maintained throughout the purification operation, despite changes in the resonant frequency of the bulb(s) 580.

According to an embodiment, the resonant circuit 590 may include a network of passive components, such as inductors, capacitors, and resistors, as described above. In a particular embodiment, the circuit 590 may include a network of variable inductors (e.g., fixed or variable inductance networks) and capacitors (e.g., fixed or variable capacitors). As used herein, the term "inductor" means a discrete inductor or a set of inductive components that are electrically coupled together without intervening components of other types (e.g., resistors or capacitors). Similarly, the term "capacitor" means a discrete capacitor, a capacitive structure formed from multiple conductive structures separated by a dielectric (e.g., air, dielectric material, or another dielectric medium) or a set of capacitive components that are electrically coupled together without intervening components of other types (e.g., resistors or inductors).

Figure 6:
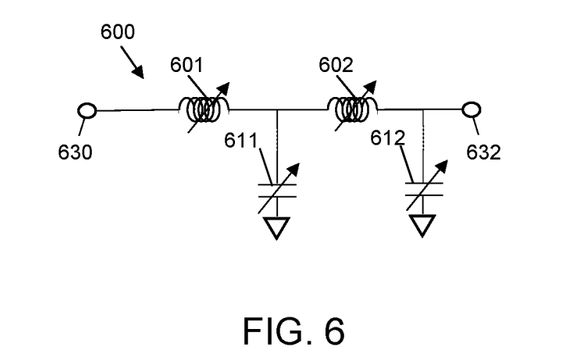
FIG. 6 is a schematic diagram of a variable resonant circuit, in accordance with an example embodiment.

FIG. 6 is a schematic diagram of a variable resonant circuit 600 that may be incorporated into a liquid purification system (e.g., system 100, 500, FIGS. 1, 5), in accordance with an example embodiment. According to an embodiment, the variable resonant circuit 600 includes a network of series-coupled inductive components that may provide inductances in a range of about 20 nanohenries (nH)

to about 400 nH, although the range may extend to lower or higher inductance values, as well.

Network 600 includes an input node 630, an output node 632, and one or more (e.g., 1, 2, or more than 2) discrete inductors 601, 602 coupled in series with each other between the input and output nodes 630, 623. In addition, network 600 includes one or more (e.g., 1, 2, or more than 2) of capacitors 611, 612, where each capacitor 611, 612 is coupled in a shunt configuration to a ground reference. Inductors 601, 602 may be implemented as discrete inductors, as distributed inductors (e.g., printed coils), as wire-bonds, or in other ways. Capacitors 611, 612 may be implemented as discrete capacitors, or may be formed from capacitive coupling between conductive system components over an air or dielectric material medium. When inductors 601, 602, capacitors 611, 612, or both are variable, the inductance or capacitance value of each component 601, 602, 611, 612 is controlled using control signals from the system controller (e.g., system controller 512, FIG. 5). For example, the control signals may be conveyed through a control path (e.g., path 516, FIG. 5).

By varying the total inductance and/or capacitance values of network 600, the system controller may move the resonant frequency of the network 600 toward or away from the resonant frequency of the electrodeless bulbs (e.g., bulbs 280, 580, FIGS. 2, 5). This may improve or degrade the resonant frequency match, where the improvement or degradation is evidenced by additional electromagnetic field intensity and/or luminous/radiation intensity measurements. In most cases, the system controller may strive to configure the network 600 in a state in which a maximum electromagnetic field intensity and/or maximum luminous/radiation intensity is achieved (i.e., a state in which the resonant frequency of the variable resonant circuit is substantially equal to the resonant frequency of the bulb).

Figure 7:
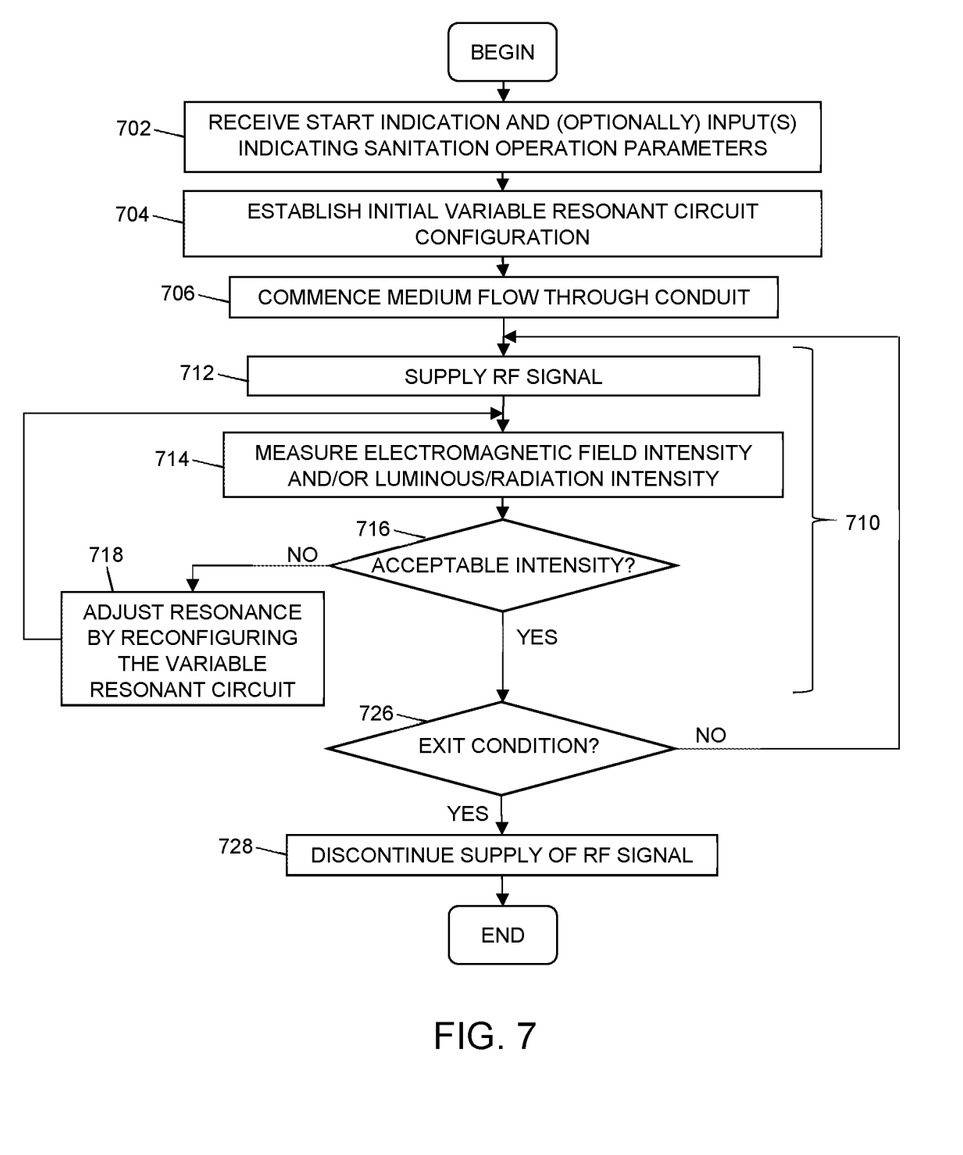
FIG. 7 is a flowchart of a method of operating a liquid purification system, in accordance with an example embodiment.

Now that embodiments of the electrical and physical aspects of electrodeless purification systems have been described, various embodiments of methods for operating such purification systems will now be described in conjunction with FIG. 7. More specifically, FIG. 7 is a flowchart of a method of operating a liquid purification system (e.g., system 100, 500, FIGS. 1, 5), in accordance with an example embodiment.

The method may begin, in block 702, when the system controller (e.g., system controller 512, FIG. 5) receives an indication that a purification operation should start. Such an indication may be received, for example, after a user has pressed a power button (e.g., of the user interface 514, FIG. 5). According to various embodiments, the system controller optionally may receive additional inputs, such as an indication of a desired duration of the purification operation, a desired excitation intensity (e.g., low, medium, or high intensity), a desired liquid flow rate, and other inputs that are relevant to the operation.

In block 704, the system controller provides control signals to the variable resonant circuit (e.g., circuit 590, FIG. 5) to establish an initial configuration or state for the variable resonant circuit. As described in detail in conjunction with FIGS. 5 and 6, the control signals affect the component values within the resonance circuit (e.g., inductances, capacitances, and/or resistances). For example, the control signals may affect the component values of the inductors 601, 602, and/or capacitors 611, 612 (FIG. 6).

Typically, at the beginning of a purification operation, as the bulb(s) begin to turn "on" and emit light or radiation, the resonant frequency of the bulb(s) is at a first frequency. Once the bulb(s) are fully "on," the resonant frequency of the bulb(s) is at a second frequency, which may be higher or lower than the first frequency. According to an embodiment, and based on the above-described, operational resonant frequency characteristics, the system controller initially sends control signals to the variable resonant circuit that configure the circuit in a state in which it has the first resonant frequency, and the system controller may send subsequent control signals to the variable resonant circuit that increase or decrease its resonant frequency as the resonant frequency of the bulb changes.

Once the initial variable resonant circuit configuration is established, in block 706, the system controller may send control signals (e.g., to pump 564, FIG. 5) to commence the flow of the medium (e.g., water, wastewater, air, and so on) through the lamp conduit (e.g., lamp conduit 130, 530, FIGS. 1, 5). The flow rate may be controlled through control signals from the system controller to the pump (e.g., pump 564, FIG. 5). Flow rate sensors (not illustrated) in the lamp conduit may provide feedback signals that enable the system controller to more finely control the flow rate.

As discussed previously, the medium to be purified flows from an input port (e.g., port 166, 566, FIGS. 1, 5), through the interior chamber (e.g., interior chamber 260, 560, FIGS. 2, 5), and out through an output port (e.g., port 168, 568, FIGS. 1, 5). As the medium flows through the interior chamber, and more specifically past the bulb(s) in the space between the electrodes and bulb(s), the UV light emitted by the bulb(s) may purify the medium by killing pathogens (e.g., bacterium, viruses, fungi, and other microorganisms) in the medium.

During the purification operation, the system controller may perform a process 710 of adjusting, if necessary, the configuration of the variable resonant circuit to find an acceptable or best match based on actual measurements that are indicative of the quality of the match. According to an embodiment, this process includes causing the RF signal source (e.g., RF signal source 520) to supply an RF signal through the variable resonant circuit to the first electrode (e.g., first electrode 240, 540, FIGS. 2, 5), in block 712. The system controller may control the RF signal power level through control signals to the power supply and bias circuitry (e.g., circuitry 526, FIG. 5), where the control signals cause the power supply and bias circuitry to provide supply and bias voltages to the amplifiers (e.g., amplifier 524, FIG. 5).

In block 714, electromagnetic field intensity, and/or luminous/radiation intensity, and/or pathogen sensor(s) (e.g., sensor 292, 592, FIGS. 2, 5) then measure the electromagnetic field intensity and/or luminous/radiation intensity and/or pathogen level within the interior chamber (e.g., interior chamber 260, 560, FIGS. 2, 5), and provide those measurements to the system controller. The system controller may then determine whether the match provided by the variable resonant circuit is acceptable (e.g., the electromagnetic field and/or luminous/radiation intensity is sufficiently high, or the pathogen level is sufficiently low). For example, the system controller may determine whether the sensed electromagnetic field intensity is above or below a threshold, and/or may determine whether the luminous/radiation intensity is above or below a threshold, and/or may determine whether the pathogen level(s) of one or more pathogens are above or below a threshold.

When the system controller determines that the match is not acceptable (e.g., the electromagnetic field and/or luminous/radiation intensity are below their associated thresholds, or the pathogen level is above its associated threshold), the system controller may adjust the match, in block 718, by reconfiguring the variable resonant circuit. For example, this may be achieved by sending control signals to the variable resonant circuit, which cause the circuit to increase and/or decrease the inductances or other component values within the circuit. This, in turn, may shift the resonant frequency of the variable resonant circuit, desirably toward the resonant frequency of the bulb(s). After reconfiguring the variable resonant circuit, blocks 714, 716, and 718 may be iteratively performed until an acceptable match between the resonant frequencies of the bulb(s) and the variable resonant circuit is determined in block 716 (or the electromagnetic field intensity and/or luminous/radiation intensity is sufficiently high, or the pathogen level is sufficiently low).

Once an acceptable match is determined or the electromagnetic field and/or luminous/radiation intensity is sufficiently high or the pathogen level is sufficiently low, the system may evaluate whether an exit condition has occurred, in block 726. In actuality, determination of whether an exit condition has occurred may be an interrupt driven process that may occur at any point during the lighting process. However, for the purposes of including it in the flowchart of FIG. 7, the process is shown to occur after block 716.

For example, the system may determine that an exit condition has occurred when a user has pressed a button indicating that the user would like the purification operation to cease. Alternatively, the system may determine that an exit condition has occurred upon expiration of a timer that was set by the user (e.g., through user interface 514, FIG. 5).

If an exit condition has not occurred, then the purification operation may continue by iteratively performing process 710. When an exit condition has occurred, then in block 728, the system controller causes the supply of the RF signal by the RF signal source to be discontinued. For example, the system controller may disable the RF signal generator (e.g., RF signal generator 520, FIG. 5) and/or may cause the power supply and bias circuitry (e.g., circuitry 526, FIG. 5) to discontinue provision of the supply current. The method may then end.

The various embodiments of electrodeless lamp-based purification systems may be incorporated into various types of liquid purification or disinfection systems, including but not limited to stand-alone water purification units, wastewater treatment systems, pool filtration and pumping systems, water heaters, reverse osmosis systems, and appliances that dispense, filter or otherwise utilize water (e.g., refrigerators, freezers, vacuum cleaners, air conditioning units, and so on). In addition, although the above description discusses systems that are configured to purify or disinfect liquids, modifications could be made to the system so that the system is configured to purify air (i.e., kill pathogens in air). For example, an embodiment of a system may be included in an air purification or disinfection system. In such an embodiment, the pump (e.g., pump 564, FIG. 5) could be replaced with a fan, and the fan could be used to force the air (or other gas) through the interior conduit.

For the sake of brevity, conventional techniques related to resonators, amplifiers, biasing, impedance matching, and other functional aspects of the systems (and the individual operating components of the systems) may not be described in detail herein. The connecting lines shown in the various figures contained herein are intended to represent exemplary functional relationships and/or physical couplings between the various elements. It should be noted that many alternative or additional functional relationships or physical connections may be present in an embodiment of the subject matter. In addition, certain terminology may also be used herein for the purpose of reference only, and thus are not intended to be limiting, and the terms "first", "second" and other such numerical terms referring to structures do not imply a sequence or order unless clearly indicated by the context.

As used herein, a "node" means any internal or external reference point, connection point, junction, signal line, conductive element, or the like, at which a given signal, logic level, voltage, data pattern, current, or quantity is present. Furthermore, two or more nodes may be realized by one physical element (and two or more signals can be multiplexed, modulated, or otherwise distinguished even though received or output at a common node).

The foregoing description refers to elements or nodes or features being "connected" or "coupled" together. As used herein, unless expressly stated otherwise, "connected" means that one element is directly joined to (or directly communicates with) another element, and not necessarily mechanically. Likewise, unless expressly stated otherwise, "coupled" means that one element is directly or indirectly joined to (or directly or indirectly communicates with) another element, and not necessarily mechanically. Thus, although the schematic shown in the figures depict one exemplary arrangement of elements, additional intervening elements, devices, features, or components may be present in an embodiment of the depicted subject matter.

A purification apparatus includes a radio frequency (RF) signal source that generates an RF signal, first and second electrodes, and a conduit. The first electrode receives the RF signal and converts it into electromagnetic energy that is radiated by the first electrode. The conduit includes input and output ports and a chamber. The input and output ports are in fluid communication with the chamber, and the chamber is configured to receive an electrodeless bulb. The chamber is defined by first and second boundaries that are separated by a distance that is less than the wavelength of the RF signal so that the chamber is sub-resonant. The first electrode is physically positioned at the first boundary, and the second electrode is physically positioned at the second boundary. The first and second electrodes and the chamber form a structure that capacitively couples the electromagnetic energy into an electrodeless bulb within the chamber.

A method of operating a purification system includes producing, by an RF signal source, an RF signal, and conveying the RF signal to a first electrode of a lamp excitation conduit that includes the first electrode, a second electrode, an input port, an output port, and an internal chamber configured to receive an electrodeless bulb. The internal chamber is defined by first and second boundaries that are separated by a distance that is less than a wavelength of the RF signal so that the internal chamber is sub-resonant. The first electrode is physically positioned at the first boundary, and the second electrode is physically positioned at the second boundary. The first electrode, the second electrode, and the internal chamber form a structure that is configured to capacitively couple the electromagnetic energy into the electrodeless bulb when the electrodeless bulb is positioned within the internal chamber. The method further includes converting, by the first electrode, the RF signal into electromagnetic energy that is radiated by the first electrode into the internal chamber, and transmitting a medium through the purification system. The medium enters the input port, passes through the internal chamber, and exits the output port.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A purification apparatus comprising:
a radio frequency (RF) signal source configured to generate a RF signal;
a first electrode electrically coupled to the RF signal source, wherein the first electrode is configured to receive the RF signal and to convert the RF signal into electromagnetic energy that is radiated by the first electrode;
a second electrode;
a conduit that includes an input port, an output port, and a chamber, wherein the input port and the output port are in fluid communication with the chamber, and the chamber is configured to receive an electrodeless bulb that has an outer diameter, and wherein the chamber is defined by first and second boundaries that are separated by a distance that is less than a wavelength of the RF signal so that the chamber is sub-resonant and that is greater than the outer diameter of the electrodeless bulb, wherein the first electrode is physically positioned at the first boundary on a first side of the chamber and, when the electrodeless bulb is positioned within the chamber, the first electrode is outside the electrodeless bulb, wherein the second electrode is physically positioned at the second boundary on a second side of the chamber opposite the first side of the chamber and, when the electrodeless bulb is positioned within the chamber, the first electrode and the second electrode are outside the electrodeless bulb and the electrodeless bulb is positioned between the first electrode and the second electrode, the input port is configured to enable a fluid or gas to flow into and through the chamber so that a first portion of the fluid or gas flows between the first electrode and the electrodeless bulb and a second portion of the fluid or gas flows between the second electrode and the electrodeless bulb and the output port is configured to enable the fluid or gas to flow out of the chamber and wherein the first electrode, the second electrode, and the chamber form a first structure that is configured to capacitively couple the electromagnetic energy into the electrodeless bulb when the electrodeless bulb is positioned within the chamber between the first and second electrodes, and the electromagnetic energy radiated by the first electrode causes the electrodeless bulb to emit ultraviolet light to kill pathogens in the fluid or gas passing through the chamber;
a support structure configured to hold the electrodeless bulb between the first electrode and the second electrode, wherein the support structure includes a clamp configured to couple to the electrodeless bulb and a post coupled at a first end of the post to the chamber and at a second end of the post to the clamp; and
a receptacle in fluid communication with the chamber, wherein the receptacle is configured to filter the pathogens in the fluid or gas.

2. The purification apparatus of claim 1, wherein the distance is less than half the wavelength of the RF signal.

3. The purification apparatus of claim 2, wherein the distance is less than one 50th the wavelength of the RF signal.

4. The purification apparatus of claim 3, wherein the distance is less than one 100th the wavelength of the RF signal.

5. The purification apparatus of claim 1, wherein the distance is in a range between 10 centimeters and 3.0 meters.

6. The purification apparatus of claim 1, wherein:
the first and second electrodes each have a planar conductive structure.

7. The purification apparatus of claim 1, further comprising:
a variable resonant circuit electrically coupled between an output of the RF signal source and the first electrode; and
a system controller configured to establish and modify a resonant frequency of the variable resonant circuit through control signals that the system controller sends to the variable resonant circuit.

8. The purification apparatus of claim 7, further comprising:
an electric field sensor configured to sense an electromagnetic field intensity within the chamber, and to send a sensor signal to the system controller indicating the electromagnetic field intensity,
wherein the system controller is configured to modify the resonant frequency of the variable resonant circuit based on the electromagnetic field intensity indicated in the sensor signal.

9. The purification apparatus of claim 7, further comprising:
a radiation intensity sensor configured to sense a radiation intensity within the chamber, and to send a sensor signal to the system controller indicating the radiation intensity,
wherein the system controller is configured to modify the resonant frequency of the variable resonant circuit based on the radiation intensity indicated in the sensor signal.

10. The purification apparatus of claim 7, further comprising:
a luminous intensity sensor configured to sense a luminous intensity within the chamber, and to send a sensor signal to the system controller indicating the luminous intensity,
wherein the system controller is configured to modify the resonant frequency of the variable resonant circuit based on the luminous intensity indicated in the sensor signal.

11. The purification apparatus of claim 7, further comprising:
a contamination sensor configured to sense a contamination level within the chamber, and to send a sensor signal to the system controller indicating the contamination level,
wherein the system controller is configured to modify the resonant frequency of the variable resonant circuit based on the contamination level indicated in the sensor signal.

12. The purification apparatus of claim 7, wherein the variable resonant circuit includes one or more variable passive devices selected from inductors, capacitors, and resistors.

13. The purification apparatus of claim 1, wherein the RF signal has a frequency in a range from 10 megahertz (MHz) to 3.0 gigahertz (GHz).

14. The purification apparatus of claim 1, wherein the RF signal source is configured to generate the RF signal to produce a voltage across the first and second electrodes in a range of 90 volts to 3000 volts.

15. The purification apparatus of claim 1, wherein the purification apparatus is selected from a water purification unit, a wastewater treatment system, an appliance that dispenses, filters or utilizes water, a pool filtration system, a pumping system, a water heater, a reverse osmosis system, a refrigerator, a freezer, a vacuum cleaner, an air conditioning unit, and an air purification system.

16. A method of operating a purification system, the method comprising:
    producing, by a radio frequency (RF) signal source, a RF signal;
    conveying the RF signal to a first electrode of a lamp excitation conduit that includes the first electrode, a second electrode, an input port, an output port, and an internal chamber configured to receive an electrodeless bulb that has an outer diameter, wherein the internal chamber is defined by first and second boundaries that are separated by a distance that is less than a wavelength of the RF signal so that the internal chamber is sub-resonant and that is greater than the outer diameter of the electrodeless bulb, wherein the first electrode is physically positioned at the first boundary on a first side of the internal chamber and, when the electrodeless bulb is positioned within the internal chamber, the first electrode is outside the electrodeless bulb, wherein the second electrode is physically positioned at the second boundary on a second side of the internal chamber opposite the first side of the internal chamber and, when the electrodeless bulb is positioned within the internal chamber, the first electrode and the second electrode are outside the electrodeless bulb and the electrodeless bulb is positioned between the first electrode and the second electrode the input port is configured to enable a fluid or gas to flow into and through the internal chamber so that a first portion of the fluid or gas flows between the first electrode and the electrodeless bulb and a second portion of the fluid or gas flows between the second electrode and the electrodeless bulb and the output port is configured to enable the fluid or gas to flow out of the internal chamber and wherein the first electrode, the second electrode, and the internal chamber form a first structure that is configured to capacitively couple an electromagnetic energy into the electrodeless bulb when the electrodeless bulb is positioned within the internal chamber between the first and second electrodes and the electromagnetic energy radiated by the first electrode causes the electrodeless bulb to emit ultraviolet light to kill pathogens in the fluid or gas passing through the internal chamber, and wherein the purification system includes a support structure configured to hold the electrodeless bulb between the first electrode and the second electrode, wherein the support structure includes a clamp configured to couple to the electrodeless bulb and a post coupled at a first end of the post to the internal chamber and at a second end of the post to the clamp, and a receptacle in fluid communication with the internal chamber, wherein the receptacle is configured to filter the pathogens in the fluid or gas;
    converting, by the first electrode, the RF signal into the electromagnetic energy that is radiated by the first electrode into the internal chamber; and
    transmitting the fluid or gas through the purification system, wherein the fluid or gas enters the input port, passes through the internal chamber, and exits the output port.

17. The method of claim 16, further comprising:
    sensing one or more of an electromagnetic field intensity within the internal chamber, a luminous intensity within the internal chamber, a radiation intensity within the internal chamber, and a contamination level in the fluid or gas;
    producing a sensor signal that indicates the electromagnetic field intensity, the luminous intensity, the radiation intensity or the contamination level; and
    modifying a resonant frequency of a variable resonant circuit that is electrically coupled between the RF signal source and the first electrode based on the sensor signal.

18. The method of claim 17, wherein modifying the resonant frequency is performed to increase the electromagnetic field intensity, increase the luminous intensity, increase the radiation intensity, or decrease the contamination level.

* * * * *